United States Patent [19]

Qianhuan

[11] Patent Number: 5,198,564

[45] Date of Patent: Mar. 30, 1993

[54] CIS-PLATINUM-DIAMINE COMPLEXES AND ANTITUMOROUS COMPOSITIONS CONTAINING THEM, AND PROCESS FOR THEIR PREPARATION

[75] Inventor: Dai Qianhuan, Beijing, China

[73] Assignees: Beijing Polytechnic University; Xingnong Technique Development Company; Beijing Agricultural University, all of Beijing, China

[21] Appl. No.: 203,041

[22] Filed: Jun. 6, 1988

[30] Foreign Application Priority Data

Jun. 5, 1987 [CN] China .................................. 87104027

[51] Int. Cl.$^5$ .............................................. C07F 15/00
[52] U.S. Cl. .................................................... 556/137
[58] Field of Search .......................... 514/492; 556/137

[56] References Cited

U.S. PATENT DOCUMENTS 4,053,587 10/1977 Davidson et al. ..................... 514/492
4,565,884 1/1986 Audrulis et al. ....................... 556/137
4,730,068 3/1988 Schonenberger et al. ........... 556/137
4,760,155 7/1988 Heffernan et al. ................... 556/137

Primary Examiner—Paul F. Shaver
Attorney, Agent, or Firm—McAulay Fisher Nissen Goldberg & Kiel

[57] ABSTRACT

The present invention relates to novel cis-platinumdiamine complexes represented by the general formula (I) and the process of preparation thereof. The definitions of the substituents in the above-mentioned formula are the same as defined in the specification. The present invention also provides antitumorous compositions containing one or more of the above-said complexes as active ingredients.

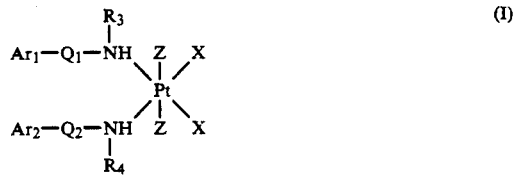

(I)

8 Claims, No Drawings

CIS-PLATINUM-DIAMINE COMPLEXES AND ANTITUMOROUS COMPOSITIONS CONTAINING THEM, AND PROCESS FOR THEIR PREPARATION

The present invention relates to derivatives of cis-platinum diamine complexes of the formula (I) which are useful as anticancer agents and compositions containing them as active ingredients. It also relates to processes of production of these complexes and compositions containing such complexes.

Cis-platinum (II) diamine dichloride (called PDD hereinafter) was incidentally discovered in 1965 (Rosenbery B. et al., Nature 205(1965)698). It was reported in 1969 that it has strong anticancer activity against Sarcoma 180 and Leukemia $L_{1210}$. The first stage of clinical experimentation was started in 1971. At the end of 1978, the Food and Drug administration of the United States of America officially approved its use as an anticancer medicine for the treatment of cancer of the testes and uterus. It was soon allowed to be used for the treatment of bladder cancer.

Although PDD is currently one of the best anticancer medicines, it has a very strong toxicity, especially to the nervous system, the stomach and the kidney. Similar to other anticancer medicines it has DNA related chronical toxicity of carcinogenesis, (Leopoled W. R., Miller E. C., Miller J. A., Cancer Res. (1979) 39 913–8) sterility and so on.

More than 1500 derivatives of PDD have been synthesized up to now, and many patents relating to PDD have been published (see, e.g. U.S. Pat. No. 4,410,544). For example, the so-called second generation of PDD, i.e., PDD derivatives, including those wherein either one or two of the amine ligands have been substituted with an alkyl group, and those wherein the chloride anion(s) have been replaced by other anion(s), have been obtained. Of these, the best is "Carboplatin" issued by Bristol-Myers Co. in 1985. However, the purpose to overcome the shortcoming that all these PDD derivatives have, namely, relatively strong carcinogenic side-effects, has not so far been achieved and this remains a problem.

The inventor, based on Di-region Theory proposed by himself (cf. Scientic Sinica (1979) 964–977) has put forward an idea of searching noncarcinogenic anti-cancer medicine [Beijing Gongye Daxue Xuebao (1985) 2. 145] and applied this idea to studying PDD congeners. Di-region Theory indicates that the key step of chemical carcinogenesis is the cross-linking between the complementary base pairs of the DNA double helix. In order to improve the selectivity and strengthen the activity of antitumor agents, when designing new antitumor agents, one should try to reduce as much as possible the ability of complementary base pairs to crosslink and at the same time to strengthen the ability to crosslink of noncomplementary base pairs as much as possible.

The present inventor has conducted extensive research on the synthesis of cis-platinum diamine complexes with a variety of substitutents. As a result a series of cis-platinum complexes has been synthesised wherein an optionally substituted alkylamine or cycloalkylamine ligand, bonded to the platinum nucleous, is substituted, on the alkyl chain or cycloalkyl ring, with optionally substituted aromatic or heteroaromatic group(s).

One of the common characteristics of the series of cis-platinum complexes, comprising the present invention, is that there exists a simple aliphatic group separating the non-aliphatic substituents, i.e. optionally substituted aromatic or heteroaromatic group(s), from the platinum nucleous thus preventing delocalisation of electrons between the substituent and the platinum nucleus.

PDD and some of its derivatives generally have low solubility in both water and organic solvents, and accordingly are poorly absorbed by the gut. Therefore, depending upon the manner of administration, the compounds sometimes exhibit low anticancer activities, and there is also a limitation for the intraperitoneal administration of such drugs for treatment purposes. Whereas it has been discovered that a number of compounds of the present invention exhibit excellent antitumorous activities in mice by a simple manner of administration and formulation, thus it is thought that the present invention may become useful in the treatment of tumors and cancers in other mammals, including humans in the future. It has been found that complexes of the present invention are novel and are not described in the literature.

The present invention of a series of cis-platinum (II) diamine complexes is represented by the general formula (I)

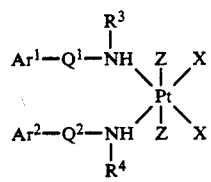

wherein
$Q^1$ and $Q^2$ which may be the same as/or different from each other, each represents aliphatic or saturated heterocyclic aliphatic divalent group;
$Ar^1$ and $Ar^2$ represent aromatic or heteroaromatic groups which may be the same as/or different from each other, or together represent a divalent aromatic or heteroaromatic group;
$R^3$ and $R^4$ may be the same as/or different from each other and represent a hydrogen atom, an alkyl group of 1 to 5 carbon atoms, a heteroalkyl group of 1 to 10 atoms; or $R^3$ and $R^4$ are such that

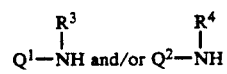

represents a saturated heterocyclic ring;
Z represents hydroxyl group which may be absent;
X represents an anionic ligand such as a halogen anion or part of a dianionic ligand, such as organic or inorganic acid residue, with the preordination that if the groups Z are absent and X is not halogen then at least one of $Ar^1$, $Q^1$ and $R^3$ must contain a heteroatom or must bear an oxygen containing group as a substituent thereon.

The present invention provides an anticancer composition containing one or more of the compounds described above as the active ingredient(s) and as well as the process for the preparation of these pharmaceutical compositions, which are also within the scope of the invention.

The following describes the terms used in the above defined formula in more detail.

The term "aliphatic or saturated heterocyclic aliphatic divalent group" means any aliphatic straight or banched alkylene group of 1 to 5 carbon atoms, or a 5, 6 or 7 membered ring, optionally containing one, two or more oxygen, nitrogen atoms in its ring such as

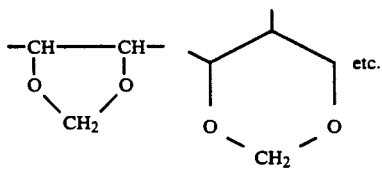

Examples of aromatic groups are optionally substituted benzene, naphthalene, phenanthrene groups with a halogen atom(s), which can be a fluorine atom, a chlorine atom, a bromine atom, or an iodine atom, a hydroxyl group(s), a nitro group(s) or a carboxyl group(s) and others as a substituent thereon.

Examples of heteroaromatic groups are optionally substituted heterocyclic groups in which at least one heteroatom is a oxygen, nitrogen or sulphur atom, and are selected from furan, pyrrole, pyridine and thiophene.

The term Examples of oxygen-containing groups are hydroxyl, hydroxymethyl, carboxymethyl and carboxyl group.

The term alkyl is intended to mean a straight-chain or branched lower alkyl group having 1-5 carbon atoms which is exemplified by methyl, ethyl, n-propyl, i-propyl, preferably a methyl group.

The term "halogen anion" represented by X means a fluorine, chlorine, bromine or iodine anion. If X represents an organic or inorganic acid residue, said acid residue may be one of the following, acetate, chloroacetate, oxalate, malonate, 1,2-benzenedicarboxylate, 4-hydroxy-1,2-benzenedicarboxylate, cyclo-1, 1-butenedicarboxylate, gluconate, sulfate etc.

The compounds of the formula (I) can be prepared, for instance, as follows:

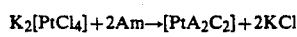

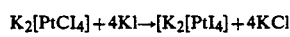

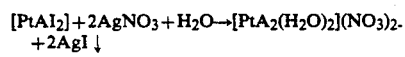

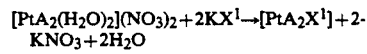

wherein $X^1$ represents any halogen atom with the exception of iodine, A represents the substituted amine ligand of the required platinum complex.

The process for the preparation of the compounds of the formula (I) comprises reacting potassium platinum chloride with a stoichiometric quantity of the substituted amine ligand of the required platinum complex in the presence of a solvent, or starting from potassium platinum chloride, converting it into the corresponding platinum diamine diiodide complex by reaction with the former with potassium iodide and then reaction the thus obtained product, i.e, potassium platinum iodide with substituted amine ligand, reacting this complex with silver nitrate to produce the corresponding hydrated complex, then converting this complex into the desired complex using the corresponding potassium halogenide, and, if necessary, further converting the obtained compound into the corresponding desired complex by reacting the former with the salt of acetic acid, chloroacetic acid, oxalatic acid, malonic acid, 1,2-benzenedicarboxylic acid, 4-hydroxy-1,2-benzene-dicarboxylic acid, cyclo-1,1-butenedicarboxylic acid, gluconic acid or sulphuric acid.

The solvents used in the above said synthetic routes may be water; alcohols having $C_{1-5}$ carbon atoms, e.g. i-propanol, n-butanol, t-butanol, n-amyl alcohol, among them ethanol being more preferred; ketones having $C_{3-5}$ carbon atoms such as acetone, methyl ethyl ketone etc. or dimethyl formamide. These solvents can be used alone or as a mixture. Among them water is preferable.

The reaction temperature can be selected in the range of 10°–50° C., and it is particularly preferable to carry out the reaction at room temperature.

The reaction time can be selected in the range of 0.5 to 24 hours. After completion of the reaction the resulting mixture is treated in a normal way. For example, the purified product can obtained by recrystallization, filtration and subsequent drying, recrystallization being not always necessary.

The preferable purifying solvents used in the purification procedure are dimethylformamide, acetone, water etc., or a mixture of these solvents.

The platinum (IV) dihydroxy complex can be obtained from the corresponding platinum (II) complex by reacting the platinum (II) complex with a 30% molar excess of hydrogenperoxide at a temperature ranging from 50° C. to 110° C.

Among the substituted amine ligands of the required platinum complex, benzyl amine, and its derivatives, may be prepared by Leuckart reaction for instance, as follows:

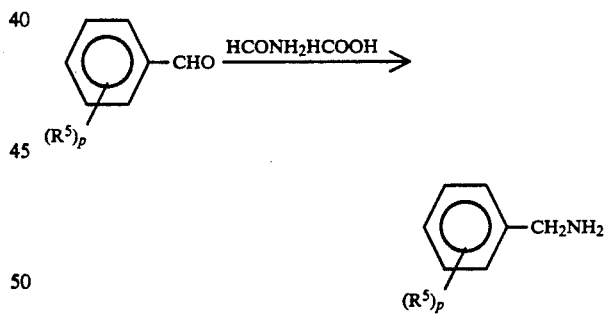

wherein $R^5$ is a halogen atom(s), which can be a fluorine, a chlorine, a bromine or a iodine atom, a hydroxyl group(s), a nitro group(s) or a carboxyl group(s).

This method is described in the literature [K. G. Lewis. J. Chem. Soc. (1950) 2249-2250] and is mainly used for synthesising aliphatic amines. When used for synthesising arylamines, for example benzyl amine, it gives a low yield of the desired product.

Adding Raney Ni as a catalyst and excess formic acid to the reaction system is an important characteristic of the present invention. The yield of such a reaction is significantly higher than that of the prior method and thus this reaction becomes industrially applicable.

Optionally substituted furanamine and hydroxybenzylamine can be prepared by reduction of the corresponding aldoxime in acidic medium as follows:

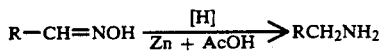

wherein R represents optionally substituted furyl or thienyl or hydroxyphenyl.

The acid used in this reaction, may be an organic or inorganic acid such as acetic acid, sulfuric acid or hydrochloric acid, etc.

Similar substituted amines, for example O-arylenedimethyleneamine can be synthesized by bromination of the corresponding starting material, followed by reaction with sodium phthalimidate and subsequent hydrolysis with hydrazine hydrate as shown below:

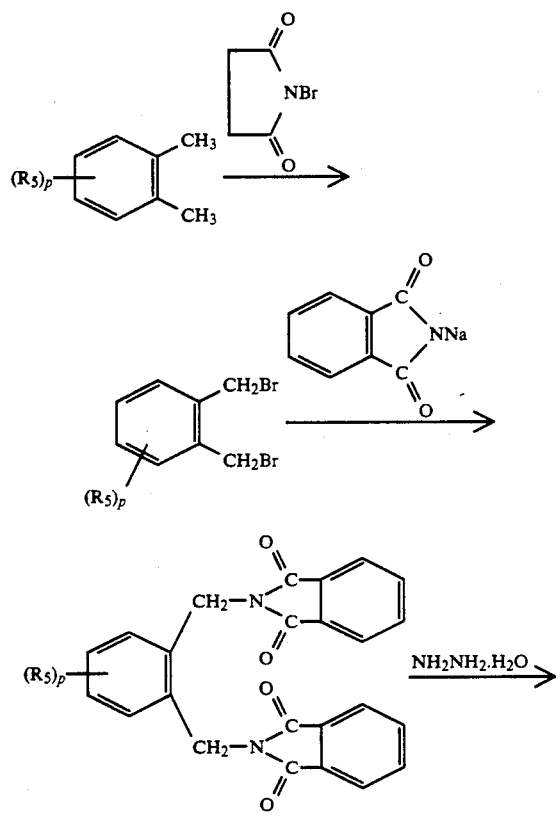

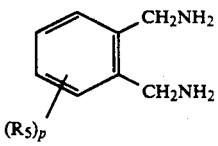

4-phenyl-5-amino-1,3-dioxane, for example, can be prepared as shown below:

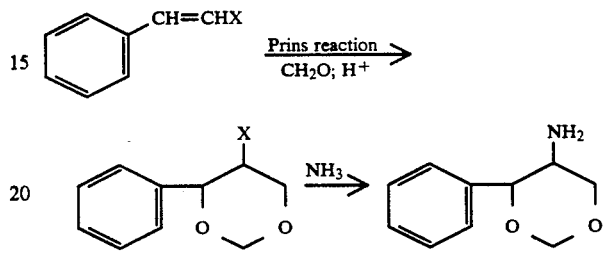

wherein X represents a chlorine or bromine atom.

The above said method was published in the following literature by the present inventor. [Dai Qianhuan, kexue tongbao 1977(9)381]

The end product is then resolved into the enantiomer by reacting it with tartaric acid followed by recrystallization in water to obtain the optical isomer of [R:R]-(-)-4-phenyl-5-amino-1,3-dioxane. The enantiomer of the above said compound can be obtained after recrystallization from methanol of the residue of the above said reaction.

This method of resolution was firstly proposed by the present inventor.

Typical examples of the compounds of the present invention represented by the general formula (I) and the solubility data thereof are shown in Tables I–IV and VI below.

TABLE 1

$$\begin{array}{c} Ar^1-Q^1-NH \\ \phantom{Ar^1-Q^1-}| \\ \phantom{Ar^1-Q^1-}R^3 \end{array} \begin{array}{c} Z \quad X \\ \backslash | / \\ Pt \\ / | \backslash \\ Z \quad X \end{array} \begin{array}{c} Ar^2-Q^2-NH \\ \phantom{Ar^2-Q^2-}| \\ \phantom{Ar^2-Q^2-}R^4 \end{array}$$

| No | Ar¹ | Ar² | Q¹ | Q² | R³ | R⁴ | X | Z | Data of element analysis or IR spectra | | |
|----|-----|-----|----|----|----|----|----|----|----|----|----|
| | | | | | | | | | | Found | Calc |
| I 1 | (2-NO₂-phenyl) | (2-NO₂-phenyl) | —CH₂— | —CH₂— | H | H | I | φ | C | 22.44 | 22.33 |
| | | | | | | | | | H | 2.21 | 2.14 |
| | | | | | | | | | N | 7.41 | 7.44 |

TABLE 1-continued

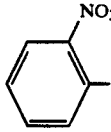

| No | Ar¹ | Ar² | Q¹ | Q² | R³ | R⁴ | X | Z | Data of element analysis or IR spectra | | |
|---|---|---|---|---|---|---|---|---|---|---|---|
| I 2 | 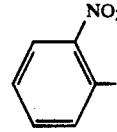 | 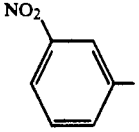 | —CH₂— | —CH₂— | H | H | Cl | φ | C<br>H<br>N | 29.33<br>2.80<br>9.65 | 29.49<br>2.81<br>9.82 |
| I 3 | 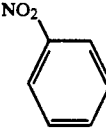 | 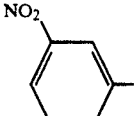 | —CH₂— | —CH₂— | H | H | I | φ | C<br>H<br>N | 22.11<br>2.02<br>7.50 | 22.32<br>2.14<br>7.44 |
| I 4 | 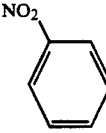 | 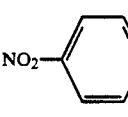 | —CH₂— | —CH₂— | H | H | Cl | φ | C<br>H<br>N | 29.39<br>2.77<br>9.74 | 29.48<br>2.81<br>9.83 |
| I 5 | 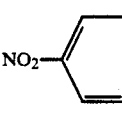 | 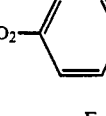 | —CH₂— | —CH₂— | H | H | I | φ | C<br>H<br>N | 22.28<br>2.19<br>7.47 | 22.32<br>2.13<br>7.44 |
| I 6 | 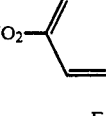 | 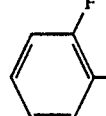 | —CH₂— | —CH₂— | H | H | Cl | φ | C<br>H<br>N | 29.55<br>2.79<br>9.76 | 29.48<br>2.81<br>9.83 |
| I 7 | 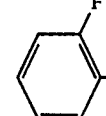 | 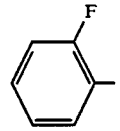 | —CH₂— | —CH₂— | H | H | I | φ | C<br>H<br>N | 24.45<br>2.31<br>3.27 | 24.04<br>2.29<br>4.01 |
| I 8 | 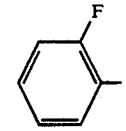 | 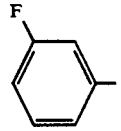 | —CH₂— | —CH₂— | H | H | Cl | φ | C<br>H<br>N | 32.43<br>2.98<br>5.21 | 32.56<br>3.10<br>5.43 |
| I 9 | 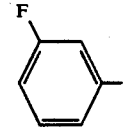 | 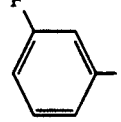 | —CH₂— | —CH₂— | H | H | I | φ | C<br>H<br>N | 23.89<br>2.19<br>4.10 | 24.04<br>2.29<br>4.01 |
| I 10 | 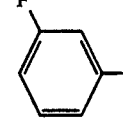 | 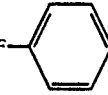 | —CH₂— | —CH₂— | H | H | Cl | φ | C<br>H<br>N | 32.51<br>3.02<br>5.48 | 32.56<br>3.10<br>5.43 |
| I 11 | 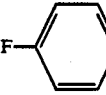 | | —CH₂— | —CH₂— | H | H | I | φ | C<br>H<br>N | 24.11<br>2.27<br>4.09 | 24.04<br>2.29<br>4.01 |

TABLE 1-continued

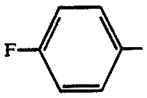

| No | Ar¹ | Ar² | Q¹ | Q² | R³ | R⁴ | X | Z | Data of element analysis or IR spectra | | |
|---|---|---|---|---|---|---|---|---|---|---|---|
| I 12 | 4-F-C₆H₄- | 4-F-C₆H₄- | —CH₂— | —CH₂— | H | H | Cl | φ | C<br>H<br>N | 32.47<br>3.05<br>5.49 | 32.56<br>3.10<br>5.43 |
| I 13 | 2-HO-C₆H₄- | 2-HO-C₆H₄- | —CH₂— | —CH₂— | H | H | I | φ | C<br>H<br>N | 24.03<br>2.41<br>4.08 | 24.19<br>2.61<br>4.03 |
| I 14 | 2-HO-C₆H₄- | 2-HO-C₆H₄- | —CH₂— | —CH₂— | H | H | Cl | φ | C<br>H<br>N | 32.80<br>3.49<br>5.44 | 32.82<br>3.52<br>5.47 |
| I 15 | 3-HO-C₆H₄- | 3-HO-C₆H₄- | —CH₂— | —CH₂— | H | H | I | φ | C<br>H<br>N | 24.21<br>2.40<br>4.15 | 24.19<br>2.61<br>4.03 |
| I 16 | 3-HO-C₆H₄- | 3-HO-C₆H₄- | —CH₂— | —CH₂— | H | H | Cl | φ | C<br>H<br>N | 32.83<br>3.49<br>5.48 | 32.82<br>3.52<br>5.47 |
| I 17 | 4-HO-C₆H₄- | 4-HO-C₆H₄- | —CH₂— | —CH₂— | H | H | I | φ | C<br>H<br>N | 24.11<br>2.51<br>4.09 | 24.18<br>2.61<br>2.03 |
| I 18 | 4-HO-C₆H₄- | 4-HO-C₆H₄- | —CH₂— | —CH₂— | H | H | Br | φ | C<br>H<br>N | 28.02<br>3.04<br>4.61 | 27.95<br>3.00<br>4.66 |
| I 19 | 4-HO-C₆H₄- | 4-HO-C₆H₄- | —CH₂— | —CH₂— | H | H | Cl | φ | C<br>H<br>N | 32.75<br>3.58<br>5.53 | 32.82<br>3.52<br>5.47 |
| I 20 | 2-Cl-4-HO-C₆H₃- | 2-Cl-4-HO-C₆H₃- | —CH₂— | —CH₂— | H | H | I | φ | C<br>H<br>N | 21.96<br>2.07<br>3.54 | 22.01<br>2.11<br>3.67 |
| I 21 | 2-Cl-4-HO-C₆H₃- | 2-Cl-4-HO-C₆H₃- | —CH₂— | —CH₂— | H | H | Cl | φ | C<br>H<br>N | 28.89<br>3.01<br>4.96 | 28.93<br>2.77<br>4.82 |

TABLE 1-continued $$Ar^1-Q^1-\underset{R^3}{NH} \underset{Z}{\overset{Z}{\underset{|}{Pt}}} \underset{X}{\overset{X}{}}$$
$$Ar^2-Q^2-\underset{R^4}{NH} \;\; Z \;\; X$$

| No | Ar¹ | Ar² | Q¹ | Q² | R³ | R⁴ | X | Z | Data of element analysis or IR spectra | | |
|---|---|---|---|---|---|---|---|---|---|---|---|
| I 22 | 4-Cl-2-hydroxyphenyl | 4-Cl-2-hydroxyphenyl | —CH₂— | —CH₂— | H | H | I | φ | C | 22.08 | 22.01 |
| | | | | | | | | | H | 2.23 | 2.11 |
| | | | | | | | | | N | 3.70 | 3.67 |
| I 23 | 4-Cl-2-hydroxyphenyl | 4-Cl-2-hydroxyphenyl | —CH₂— | —CH₂— | H | H | Cl | φ | C | 28.42 | 28.93 |
| | | | | | | | | | H | 2.81 | 2.77 |
| | | | | | | | | | N | 4.79 | 4.82 |
| I 24 | 2,3,5-trihydroxyphenyl | 2,3,5-trihydroxyphenyl | —CH₂— | —CH₂— | H | H | I | φ | C | 22.24 | 22.15 |
| | | | | | | | | | H | 2.26 | 2.39 |
| | | | | | | | | | N | 3.76 | 3.69 |
| I 25 | 2,3,5-trihydroxyphenyl | 2,3,5-trihydroxyphenyl | —CH₂— | —CH₂— | H | H | Cl | φ | C | 29.08 | 29.18 |
| | | | | | | | | | H | 3.11 | 3.15 |
| | | | | | | | | | N | 4.74 | 4.86 |
| I 26 | 2-COOH-5-hydroxyphenyl | 2-COOH-5-hydroxyphenyl | —CH₂— | —CH₂— | H | H | I | φ | C | 24.60 | 24.54 |
| | | | | | | | | | H | 3.36 | 2.32 |
| | | | | | | | | | N | 3.52 | 3.58 |
| I 27 | 2-COOH-5-hydroxyphenyl | 2-COOH-5-hydroxyphenyl | —CH₂— | —CH₂— | H | H | Cl | φ | C | 32.07 | 32.01 |
| | | | | | | | | | H | 3.26 | 3.02 |
| | | | | | | | | | N | 4.63 | 4.67 |
| I 28 | [phenyl-C(H)(CH₃)] | [phenyl-C(H)(CH₃)] | —CH(CH₃)— | —CH(CH₃)— | H | H | I | φ | yellow 3260, 3215, 3180, 1560, 1485, 1445, 1190, 1160, 760, 695, 430, | | |
| I 29 | [phenyl-C(H)(CH₃)] | [phenyl-C(H)(CH₃)] | —CH(CH₃)— | —CH(CH₃)— | H | H | Cl | φ | yellow 3250, 3190, 3105, 2960, 1640, 1560, 1490, 1445, 1275, 1185, 1070, 750, 695, 545, 500, 490, | | |
| I 30 | [phenyl-C(H)(CH₃)] | [phenyl-C(H)(CH₃)] | —CH(CH₃)— | —CH(CH₃)— | H | H | I | φ | yellow 3260, 3215, 3180, 1560, 1485, 1445, 1190, 1160, 745, 630, | | |

TABLE 1-continued $$Ar^1-Q^1-NH(R^3) \underset{Z}{\overset{Z}{\diagdown}} Pt \underset{Z}{\overset{X}{\diagdown}} X$$
$$Ar^2-Q^2-NH(R^4)$$

| No | Ar¹ | Ar² | Q¹ | Q² | R³ | R⁴ | X | Z | Data of element analysis or IR spectra | | |
|---|---|---|---|---|---|---|---|---|---|---|---|
| I 31 | [phenyl-C(H)(CH₃)-] | [phenyl-C(H)(CH₃)-] | CH₃ −CH− | CH₃ −CH− | H | H | Cl | φ | yellow 3250, 3190, 3105, 2960, 1560, 1490, 1445, 1325, 1185, 1070, 750, 695, 545, 500, 490, | | |
| | | | | | | | | | | Found | Calc. |
| I 32 | 2-COOH-phenyl | 2-COOH-phenyl | −CH₂− | −CH₂− | H | H | I | φ | C | 25.41 | 25.58 |
| | | | | | | | | | H | 2.39 | 2.42 |
| | | | | | | | | | N | 3.69 | 3.73 |
| I 33 | 2-COOH-phenyl | 3-COOH-phenyl | −CH₂− | −CH₂− | H | H | Cl | φ | C | 33.76 | 33.81 |
| | | | | | | | | | H | 3.15 | 3.19 |
| | | | | | | | | | N | 4.97 | 4.93 |
| I 34 | 3-COOH-phenyl | 3-COOH-phenyl | −CH₂− | −CH₂− | H | H | I | φ | C | 25.61 | 25.58 |
| | | | | | | | | | H | 2.55 | 2.42 |
| | | | | | | | | | N | 3.82 | 3.73 |
| I 35 | 3-COOH-phenyl | 3-COOH-phenyl | −CH₂− | −CH₂− | H | H | Cl | φ | C | 33.85 | 33.81 |
| | | | | | | | | | H | 3.24 | 3.19 |
| | | | | | | | | | N | 4.90 | 4.93 |
| I 36 | 4-HOOC-phenyl | 4-HOOC-phenyl | −CH₂− | −CH₂− | H | H | I | φ | C | 25.26 | 25.58 |
| | | | | | | | | | H | 2.43 | 2.42 |
| | | | | | | | | | N | 3.75 | 3.73 |
| I 37 | 4-HOOC-phenyl | 4-HOOC-phenyl | −CH₂− | −CH₂− | H | H | Cl | φ | C | 33.90 | 33.81 |
| | | | | | | | | | H | 3.21 | 3.19 |
| | | | | | | | | | N | 4.85 | 4.93 |
| I 38 | 5-Cl-2-COOH-phenyl | 5-Cl-2-COOH-phenyl | −CH₂− | −CH₂− | H | H | I | φ | C | 23.40 | 23.43 |
| | | | | | | | | | H | 1.85 | 1.97 |
| | | | | | | | | | N | 3.38 | 3.42 |
| I 39 | 3-Cl-2-COOH-phenyl | 3-Cl-2-COOH-phenyl | −CH₂− | −CH₂− | H | H | Cl | φ | C | 30.29 | 30.16 |
| | | | | | | | | | H | 2.45 | 2.53 |
| | | | | | | | | | N | 4.33 | 4.40 |
| I 40 | 2,4-(HOOC)₂-phenyl | 2,4-(HOOC)₂-phenyl | −CH₂− | −CH₂− | H | H | I | φ | C | 25.69 | 25.76 |
| | | | | | | | | | H | 2.15 | 2.16 |
| | | | | | | | | | N | 3.28 | 3.34 |

TABLE 1-continued $$\begin{array}{c} \text{Ar}^1-\text{Q}^1-\overset{\text{R}^3}{\underset{|}{\text{N}}}\text{H} \underset{Z}{\overset{Z}{\diagdown}}\underset{X}{\overset{X}{\diagup}} \\ \text{Pt} \\ \text{Ar}^2-\text{Q}^2-\underset{|}{\text{N}}\text{H} \underset{Z}{\overset{Z}{\diagup}}\underset{X}{\overset{X}{\diagdown}} \\ \overset{|}{\text{R}^4} \end{array}$$

| No | Ar¹ | Ar² | Q¹ | Q² | R³ | R⁴ | X | Z | Data of element analysis or IR spectra |
|---|---|---|---|---|---|---|---|---|---|
| I 41 | 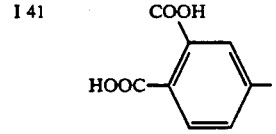 | 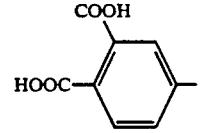 | —CH₂— | —CH₂— | H | H | Cl | φ | C 32.90 32.94<br>H 2.61 2.76<br>N 4.21 4.27 |
| I 42 | 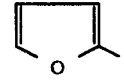 | 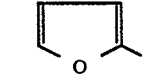 | —CH₂— | —CH₂— | H | H | I | φ | yellow 3230, 3175, 3100, 1565, 1490, 1135, 1240, 1210, 1140, 965, 810, 735, 600 |
| I 43 | 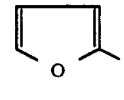 | 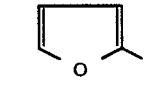 | —CH₂— | —CH₂— | H | H | Cl | φ | yellow 3220, 3190, 3120, 1565, 1490, 1430, 1360, 1240, 1220, 1140, 1000, 970, 735, 600 |
|  |  |  |  |  |  |  |  |  | Found Calc. |
| I 44 | 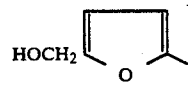 | 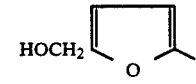 | —CH₂— | —CH₂— | H | H | I | φ | C 20.58 20.50<br>H 2.49 2.58<br>N 3.95 3.98 |
| I 45 | 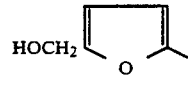 | 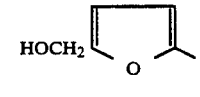 | —CH₂— | —CH₂— | H | H | Cl | φ | C 27.81 27.70<br>H 3.41 3.49<br>N 5.35 5.38 |
| I 46 | 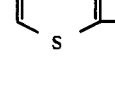 | 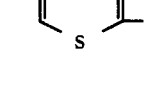 | —CH₂— | —CH₂— | H | H | I | φ | C 17.83 17.79<br>H 2.05 2.09<br>N 4.21 4.15 |
| I 47 | 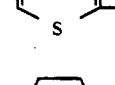 | 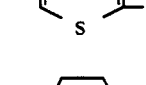 | —CH₂— | —CH₂— | H | H | Cl | φ | C 24.37 24.40<br>H 2.91 2.87<br>N 5.73 5.69 |
| I 48 | 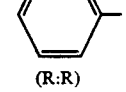<br>(R:R) | 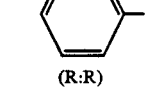<br>(R:R) | 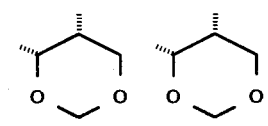 | 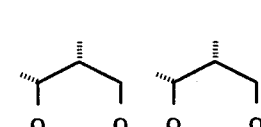 | H | H | I | φ | yellow 3260, 3180, 3100, 2845, 1570, 1440, 1350, 1215, 1160, 1050, 1000, 960, 810, 730, 690, 575, 520, 430 |
| I 49 | <br>(R:R) | <br>(R:R) | 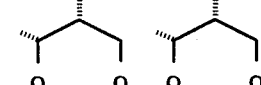 | 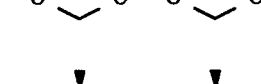 | H | H | Cl | φ | yellow 3280, 3200, 3110, 2860, 1660, 1575, 1450, 1170, 1065, 1015, 970, 895, 740, 700, 580, 530, 445 |
| I 50 | 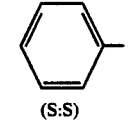<br>(S:S) | 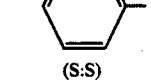<br>(S:S) | 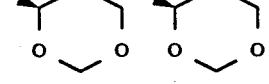 |  | H | H | I | φ | yellow 3260, 3180, 3100, 2845, 1570, 1440, 1350, 1215, 1160, 1050, 1000, 960, 810, 730, 690, 575, 520, 430 |
| I 51 | 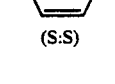<br>(S:S) | 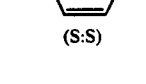<br>(S:S) | 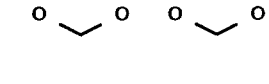 |  | H | H | Cl | φ | yellow 3280, 3200, 2860, 1660, 1575, 1450, 1165, 1065, 1015, 970, 895, 740, 700, 580, 530, 445 |
|  |  |  |  |  |  |  |  |  | Found Calc. |

TABLE 1-continued $$Ar^1-Q^1-NH(R^3) \quad Z \quad X$$
$$\quad\quad\quad\quad\quad Pt$$
$$Ar^2-Q^2-NH(R^4) \quad Z \quad X$$

| No | Ar¹ | Ar² | Q¹ | Q² | R³ | R⁴ | X | Z | Data of element analysis or IR spectra | | |
|---|---|---|---|---|---|---|---|---|---|---|---|
| I 52 | phenyl | phenyl | -CH(OH)-CH₂- | -CH(CH)-CH₂- | H | H | I | φ | C<br>H<br>N | 26.39<br>3.15<br>3.61 | 26.57<br>3.07<br>3.87 |
| I 53 | phenyl | phenyl | -CH(OH)-CH₂- | -CH(OH)CH₂- | H | H | Cl | φ | C<br>H<br>N | 35.43<br>3.99<br>5.04 | 35.56<br>4.10<br>5.18 |
| I 54 | HOOCCH₂-C₆H₄- | HOOCCH₂-C₆H₄- | -CH₂- | -CH₂- | H | H | I | φ | C<br>H<br>N | 27.92<br>3.01<br>3.47 | 27.74<br>2.85<br>3.59 |
| I 55 | HOOCCH₂-C₆H₄- | HOOCCH₂-C₆H₄- | -CH₂- | -CH₂- | H | H | Cl | φ | C<br>H<br>N | 36.51<br>3.76<br>4.82 | 36.25<br>3.72<br>4.70 |

TABLE II

Structure:
$$Ar^1-Q^1-NH(R^3) \quad Z \quad X$$
$$\quad\quad\quad\quad\quad Pt$$
$$Ar^2-Q^2-NH(R^4) \quad Z \quad X$$

| No | Ar¹ = AR² = Ar | Q¹ | Q² | R³ | R⁴ | X | Z | data of element analysis Or IR Spectra |
|---|---|---|---|---|---|---|---|---|
| II 1 | 2-methylphenyl | -CH₂- | -CH₂- | H | H | I | φ | 3240, 3220, 3170, 1555, 1445, 1380, 1210, 1180, 970, 740, 655, 510, 450 |
| II 2 | 2-methylphenyl | -CH₂- | -CH₂- | H | H | Cl | φ | 3250, 3220, 3170, 3100, 1640, 1575, 1470, 1450, 1370, 1285, 1215, 1190, 1170, 1155, 1090, 975, 790, 750, 600, 525 |
| II 3 | 4-chloro-2-methylphenyl | -CH₂- | -CH₂- | H | H | I | φ | 3240, 3220, 3180, 3160, 3080, 1645, 1555, 1486, 1465, 1410, 1370, 1200, 1160, 1005, 870, 825, 655 |
| II 4 | 4-chloro-2-methylphenyl | -CH₂- | -CH₂- | H | H | Cl | φ | 3220, 3190, 3100, 1590, 1565, 1480, 1325, 1220, 1110, 870, 825, 655, 540 |
| II 5 | 4-bromo-2-methylphenyl | -CH₂- | -CH₂- | H | H | I | φ | 3230, 3222, 3160, 3080, 1650, 1585, 1560, 1475, 1400, 1370, 1200, 1155, 1100, 865, 830, 655, 600 |

TABLE II-continued

Structure:

$$Ar^1-Q^1-NH(R^3)\diagdown_{Pt}\diagup^{Z-X}_{Z-X}$$
$$Ar^2-Q^2-NH(R^4)\diagup$$

| No | Ar¹ = AR² = Ar | Q¹ | Q² | R³ | R⁴ | X | Z | data of element analysis Or IR Spectra | | |
|---|---|---|---|---|---|---|---|---|---|---|
| II 6 | 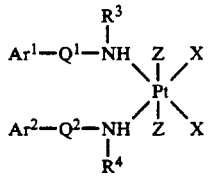 | —CH₂— | —CH₂— | H | H | Cl | φ | 3220, 3170, 3100, 1650, 1640, 1585, 1565, 1495, 1405, 1380, 1360, 1200, 1195, 1170, 1100, 1090, 960, 870, 820, 655, 550, 420 | | |
| | | | | | | | | | Found | Calc |
| II 7 | 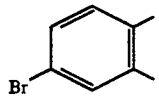 | —CH₂— | —CH₂— | H | H | I | φ | C<br>H<br>N | 15.97<br>1.90<br>4.71 | 15.93<br>1.84<br>4.64 |
| II 8 | 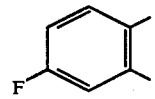 | —CH₂— | —CH₂— | H | H | Cl | φ | C<br>H<br>N | 22.76<br>2.59<br>6.57 | 22.87<br>2.64<br>6.67 |
| II 9 | 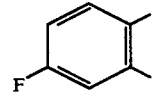 | —CH₂— | —CH₂— | H | H | I | φ | C<br>H<br>N | 17.32<br>1.97<br>4.46 | 17.18<br>1.92<br>4.45 |
| II 10 | 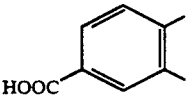 | —CH₂— | —CH₂— | H | H | Cl | φ | C<br>H<br>N | 24.09<br>2.77<br>6.35 | 24.23<br>2.71<br>6.28 |
| II 11 |  | —CH— | —CH— | H | H | Cl | φ | C<br>H<br>N | 22.32<br>1.91<br>4.35 | 22.20<br>1.86<br>4.32 |
| II 12 | 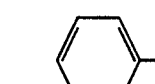 | —CH— | —CH— | H | H | I | φ | C<br>H<br>N | 30.87<br>2.63<br>6.04 | 30.91<br>2.59<br>6.01 |
| II 13 |  | —CH— | —CH— | H | H | Cl | φ | C<br>H<br>N | 25.67<br>1.81<br>3.70 | 25.72<br>1.89<br>3.75 |

TABLE II-continued

Structure:
$$Ar^1-Q^1-NH(R^3)\diagdown Pt(Z|X)(Z|X) \diagup NH(R^4)-Q^2-Ar^2$$

| No | Ar¹ = AR² = Ar | Q¹ | Q² | R³ | R⁴ | X | Z | data of element analysis Or IR Spectra | | |
|---|---|---|---|---|---|---|---|---|---|---|
| II 14 | 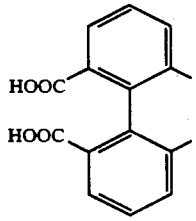 | −CH−<br>\| | −CH−<br>\| | H | H | I | φ | C<br>H<br>N | 34.01<br>2.54<br>4.89 | 34.06<br>2.50<br>4.96 |

TABLE III

Structure:
$$Ar^1-Q^1-NH(R^3)\diagdown Pt(Z|X)(Z|X) \diagup NH(R^4)-Q^2-Ar^2$$

| No | Ar¹ | Ar² | Q¹ | Q² | R³ | R⁴ | X | Z | Data of element or IR spectra | | |
|---|---|---|---|---|---|---|---|---|---|---|---|
| | | | | | | | | | | | Calc |
| III 1 | 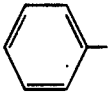 | 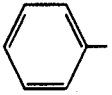 | −CH₂− | −CH₂− | H | H | Cl | OH | C<br>H<br>N<br>Cl | 33.82<br>3.87<br>5.57<br>13.57 | 32.69<br>3.92<br>5.45<br>13.79 |
| III 2 | 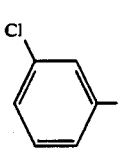 Cl | 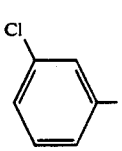 Cl | −CH₂− | −CH₂− | H | H | Cl | OH | C<br>H<br>N<br>Cl | 29.04<br>2.97<br>4.85<br>24.62 | 28.83<br>3.11<br>4.80<br>24.32 |
| III 3 | 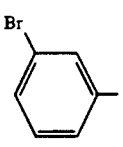 Br | 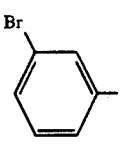 Br | −CH₂− | −CH₂− | H | H | Cl | OH | C<br>H<br>N | 25.49<br>2.59<br>4.13 | 25.02<br>2.68<br>4.17 |
| III 4 | 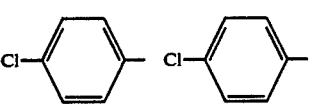 Cl | 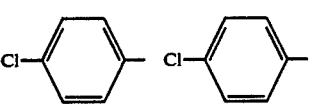 Cl | −CH₂− | −CH₂− | H | H | Cl | OH | C<br>H<br>N | 28.79<br>3.02<br>4.78 | 28.83<br>3.11<br>4.80 |
| III 5 | 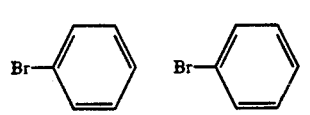 Br | 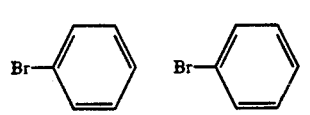 Br | −CH₂− | −CH₂− | H | H | Cl | OH | C<br>H<br>N | 25.27<br>2.62<br>4.21 | 25.02<br>2.70<br>4.17 |
| III 6 | 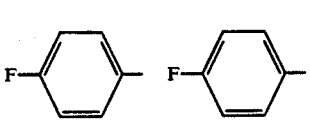 F | 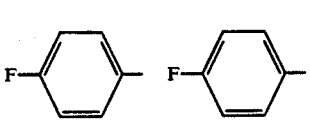 F | −CH₂− | −CH₂− | H | H | Cl | OH | C<br>H<br>N | 30.38<br>3.30<br>5.14 | 30.56<br>3.30<br>5.09 |

TABLE IV

Structure:
$$Ar^1-Q^1-NH(R^3)\diagdown_{Z}^{Z}Pt_{Z}^{X}\diagup X$$
$$Ar^2-Q^2-NH(R^4)\diagup$$

| No | Ar¹ | Ar² | Q¹ | Q² | R³ | R⁴ | X | Z | Data of element analysis O IR spectra Found | Calc |
|---|---|---|---|---|---|---|---|---|---|---|
| IV 1 | 4-Cl-C₆H₄- | 4-Cl-C₆H₄- | $-CH_2-$ | $-CH_2-$ | H | H | ½[$CO_2^-$–$CO_2^-$] (oxalate) | O | C 33.72  H 2.78  N 4.92 | 33.94  2.85  4.95 |
| IV 2 | 4-Cl-C₆H₄- | 4-Cl-C₆H₄- | $-CH_2-$ | $-CH_2-$ | H | H | ½[$CH_2(CO_2^-)_2$] (malonate) | O | C 35.34  H 3.20  N 4.85 | 35.18  3.13  4.83 |
| IV 3 | 4-Cl-C₆H₄- | 4-Cl-C₆H₄- | $-CH_2-$ | $-CH_2-$ | H | H | $ClCH_2COO^-$ | O | C 33.01  H 3.08  N 4.17 | 32.50  3.03  4.21 |
| IV 4 | 4-Cl-C₆H₄- | 4-Cl-C₆H₄- | $-CH_2-$ | $-CH_2-$ | H | H | ½ $SO_4$ | O | C 30.16  H 2.87  N 4.56 | 29.28  2.81  4.88 |
| IV 5 | C₆H₅- | C₆H₅- | $-CH_2-$ | $-CH_2-$ | H | H | ½[4-OH-C₆H₃(CO₂)₂] | O | C 44.72  H 3.71  N 4.80 | 44.82  3.76  4.75 |
| IV 6 | 2-furyl | 2-furyl | $-CH_2-$ | $-CH_2-$ | H | H | ½[$CH_2(CO_2)_2$] | O | C 32.02  H 3.21  N 5.76 | 31.78  3.28  5.70 |
| IV 7 | 4-Cl-C₆H₄- | 4-Cl-C₆H₄- | $-CH_2-$ | $-CH_2-$ | H | H | ½ [1,1-cyclobutanedicarboxylate] | O | C 38.63  H 3.39  N 4.48 | 38.72  3.57  4.52 |
| IV 8 | 4-F-C₆H₄- | 4-F-C₆H₄- | $-CH_2-$ | $-CH_2-$ | H | H | ½ [1,1-cyclobutanedicarboxylate] | O | C 40.80  H 3.84  N 4.67 | 40.89  3.77  4.77 |
| IV 9 | 2-furyl | 2-furyl | $-CH_2-$ | $-CH_2-$ | H | H | ½ [1,1-cyclobutanedicarboxylate] | O | C 36.25  H 3.83  N 5.19 | 36.16  3.79  5.27 |

TABLE VI(a)

Solubility of Platinum Complexes

| Structure (Cis) | Solubility (mg/ml, H₂O) |
|---|---|
| cis-Pt(NH₃)₂Cl₂ | 2.5 |
| cis-Pt(NH₃)₂(1,1-cyclobutanedicarboxylate) | 18.5 |

TABLE VI(a)-continued

Solubility of Platinum Complexes

| Structure (Cis) | Solubility (mg/ml, H$_2$O) |
|---|---|
| 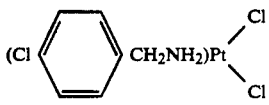 (Cl⟨phenyl⟩CH$_2$NH$_2$)Pt(Cl)(Cl) | 0.01 |
| 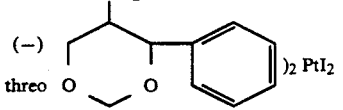 (−) threo, NH$_2$, O-CH$_2$-O, phenyl, )$_2$ PtI$_2$ | 0.02 |
| 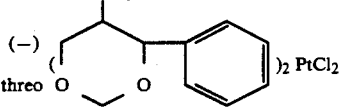 (−) threo, NH$_2$, O-CH$_2$-O, phenyl, )$_2$ PtCl$_2$ | 0.06 |
| 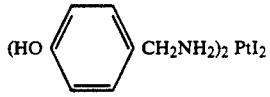 (HO⟨phenyl⟩CH$_2$NH$_2$)$_2$ PtI$_2$ | 0.8 |
| 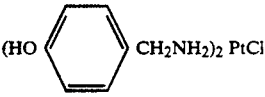 (HO⟨phenyl⟩CH$_2$NH$_2$)$_2$ PtCl$_2$ | 1.5 |
| 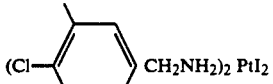 (Cl⟨phenyl-OH⟩CH$_2$NH$_2$)$_2$ PtI$_2$ | 0.4 |
| 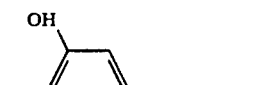 (Cl⟨phenyl-OH⟩CH$_2$NH$_2$)$_2$ PtCl$_2$ | 0.9 |
|  (HOOC⟨phenyl⟩CH$_2$NH$_2$)$_2$ PtI$_2$ | 1.0 |
| 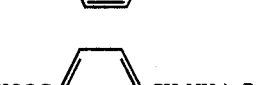 (HOOC⟨phenyl⟩CH$_2$NH$_2$)$_2$ PtCl$_2$ | 2.2 |
|  (⟨furan⟩CH$_2$NH$_2$)$_2$ PtI$_2$ | 0.06 |
|  (⟨furan⟩CH$_2$NH$_2$)$_2$ PtCl$_2$ | 0.16 |
| 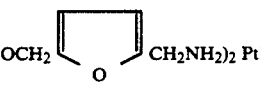 (HOCH$_2$⟨furan⟩CH$_2$NH$_2$)$_2$ PtI$_2$ | 0.2 |
| 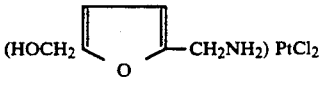 (HOCH$_2$⟨furan⟩CH$_2$NH$_2$) PtCl$_2$ | 1.1 |

TABLE VI(a)-continued

Solubility of Platinum Complexes

| Structure (Cis) | Solubility (mg/ml, H$_2$O) |
|---|---|
| 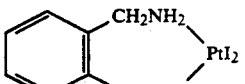 benzene with two CH$_2$NH$_2$ groups, PtI$_2$ | 0.01 |
| 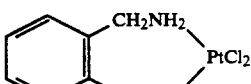 benzene with two CH$_2$NH$_2$ groups, PtCl$_2$ | 0.02 |
| 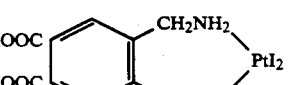 HOOC, HOOC-benzene with two CH$_2$NH$_2$ groups, PtI$_2$ | 1.1 |
| 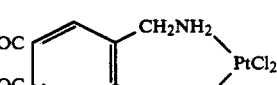 HOOC, HOOC-benzene with two CH$_2$NH$_2$ groups, PtCl$_2$ | 2.4 |

The results of the tests for the anticancer effects of the compounds according to the present invention are summarized in Table V.

Extensive research has shown that as compared with PDD, the compounds of the present invention particularly those listed in Tables I, II, III, IV, and V, display a higher effect in prolonging the life of mouse with cancer (tumor) which includes a great number of different mammalian types of tumor in mice, such as L$_{1210}$ lymphoid leukemia (LE), B$_{16}$ melanocarcinoma, Hela uterus carcinoma and gastric cancer cell MGC-803. Therefore, at least the compounds listed in Table V are useful as the curative agents for S$_{180}$ sarcoma and L$_{1210}$ mouse leukemia (LE) in mice.

EFFECT IN PROLONGING THE LIFE OF MOUSE WITH CANCER (L$_{1210}$)

Test Example 1

To DBA/2 mice, L$_{1210}$ mouse leukemia cells were inoculated into the abdominal cavity of each mouse used in the test. The test drugs were intraperitoneally administered once (e.g. after 24 hours of inoculation). The mice were observed for 30 days for survival or death. The ratio (T/C %) of the survival time of a treated group (administered with a certain drug) to the survival time of a control group (administered with only physiological saline) was obtained and is shown in table VI with the average number of survival days for mice of the control group being evaluated as 100. The test drugs were aqueous suspensions obtained by adding small amounts of surfactants (e.g. tween-80) to the less soluble test compounds in water.

EFFECT IN PROLONGING THE LIFE OF MOUSE WITH CANCER (S$_{180}$)

Test Example 2

To DBA/2 mice, S$_{180}$ sarcoma cells were intraperitoneally inoculated with approximately 1×10$^6$ cells/mouse. The test drugs were intraperitoneally administered once (e.g. after 24 hours of inoculation). The mice were observed for 30 days for survival or death. The ratio (T/C %) of survival time of test and control animals was obtained and is shown in table V with the average number of survival days for mice of the control group to which a physiological saline was administered being evaluated as 100. The test drugs were aqueous suspensions obtained by adding small amount of surfactants (e.g. tween-80) to the less soluble test compounds in water.

TABLE V

| No | compounds — The substituted amino ligand of the required platinum complex | The acid residue | Kinds of carcinomia cells | Dose of test compd mg/kg | T/C (%) of ST[1] |
|---|---|---|---|---|---|
| comparative compound | Cis-PDD | | L1210<br>S180 | 3.5<br>3.5 | 132<br>140 |
| I 11 | F—C6H4—CH2NH2 | I | L1210<br>S180 | 13.5<br>13.5 | >161<br>>184 |
| I 12 | F—C6H4—CH2NH2 | Cl | L1210<br>S180 | 13.5<br>13.5 | >177<br>>175 |
| I | Cl—C6H4—CH2NH2 | I | L1210<br>S180 | 10<br>10 | >182<br>>140 |
| I | Cl—C6H4—CH2NH2 | Cl | L1210<br>S180 | 10<br>10 | >197<br>>140 |
| V/7 | Cl—C6H4—CH2NH2 | $CO_2$—cyclobutane—$CO_2$ | L1210<br>S180 | 10<br>10 | >210<br>>202 |
| I | C6H5—CH2NH2 | I | L1210<br>S180 | 8 | >201 |
| I | C6H5—CH2NH2 | Cl | L1210<br>S180 | 8 | >201 |
| I 28 | [R]C6H5CH(CH3)NH2 | I | L1210<br>S180 | 17.5<br>17.5 | >220<br>>215 |
| I 29 | [R]C6H5CH(CH3)NH2 | Cl | L1210<br>S180 | 17.5<br>17.5 | >246<br>>250 |
| I 30 | [S]C6H5CH(CH3)NH2 | I | L1210<br>S180 | 17.5<br>17.5 | >226<br>>230 |
| I 31 | [S]C6H5CH(CH3)NH2 | Cl | L1210<br>S180 | 17.5<br>17.5 | >260<br>>245 |

TABLE V-continued

| No | The substituted amino ligand of the required platinum complex | The acid residue | Kinds of carcinomia cells | Dose of test compd mg/kg | T/C (%) of ST[1] |
|---|---|---|---|---|---|
| I 20 | OH, Cl, CH₂NH₂ (phenyl) | I | L1210<br>S180 | 15<br>15 | >212<br>>227 |
| I 21 | OH, Cl, CH₂NH₂ (phenyl) | Cl | L1210<br>S180 | 15<br>15 | >238<br>>251 |
| I 36 | HOOC—C₆H₄—CH₂NH₂ | I | L1210<br>S180 | 10<br>10 | >243<br>>230 |
| I 37 | HOOC—C₆H₄—CH₂NH₂ | Cl | L1210<br>S180 | 10<br>10 | >250<br>>255 |
| I | Br, CH₂NH₂ (phenyl, 2-Br) | I | L1210<br>S180 | 10<br>10 | >175<br>>180 |
| I | Br, CH₂NH₂ (phenyl, 2-Br) | Cl | L1210<br>S180 | 10<br>10 | >180<br>>184 |
| I | Br—C₆H₄—CH₂NH₂ | I | L1210<br>S180 | 17.5<br>17.5 | >150<br>>158 |
| I | Br—C₆H₄—CH₂NH₂ | Cl | L1210<br>S180 | 12<br>12 | >205<br>>198 |
| I 42 | furan-CH₂NH₂ | I | L1210<br>S180 | 17.5<br>17.5 | >200<br>>200 |
| I 43 | furan-CH₂NH₂ | Cl | L1210<br>S180 | 12<br>12 | >225<br>>230 |
| I 44 | HOCH₂-furan-CH₂NH₂ | I | L1210<br>S180 | 17.5<br>17.5 | >215<br>>220 |
| I 45 | HOCH₂-furan-CH₂NH₂ | Cl | L1210<br>S180 | 12<br>12 | >226<br>>218 |

TABLE V-continued

| No | compounds — The substituted amino ligand of the required platinum complex | The acid residue | Kinds of carcinomia cells | Dose of test compd mg/kg | T/C (%) of ST[1] |
|---|---|---|---|---|---|
| I 48 | [R:R] phenyl-NH2 with O-CH2-O dioxolane | I | L1210 S180 | 17.5 17.5 | >168 >175 |
| I 49 | [R:R] phenyl-NH2 with O-CH2-O dioxolane | Cl | L1210 S180 | 12 12 | >203 >207 |
| I 50 | [S:S] phenyl-NH2 with O-CH2-O dioxolane | I | L1210 S180 | 17.5 17.5 | >190 >198 |
| I 51 | [S:S] phenyl-NH2 with O-CH2-O dioxolane | Cl | L1210 S180 | 12 12 | >215 >211 |
| III 1 | o-bis(CH2NH2)benzene | I | L1210 S180 | 17.5 17.5 | >140 >135 |
| III 2 | o-bis(CH2NH2)benzene | Cl | L1210 S180 | 10 10 | >196 >202 |
| III 9 | HOOC-phenyl-bis(CH2NH2) | I | L1210 S180 | 10 10 | >184 >176 |
| III 10 | HOOC-phenyl-bis(CH2NH2) | Cl | L1210 S180 | 10 10 | >212 >215 |
| V 4 | Cl-phenyl-CH2NH2 (2, OH) | Cl | L1210 S180 | 10 10 | >252 >260 |

Notes:
ST[1] Ratio of survival time of test and control animals.

The compounds of this invention are expected to serve as antitumorous agents as described above. According to the different reactivity of the anion in these compounds, they can be administered either orally, parenterally such as subcutaneously, introvenously, intramuseularly or intraperatoneally or rectally.

The content of some compounds of present invention in piece of medicament may vary over a wide range according to the form of the medicament and other factors, but usually it is contained in a ratio of 0.01 to 100%, preferably 0.1 to 70% (by weight), the rest of the medicament comprising the carrier and other adjuvants.

As to the dose, said compounds should be administered continuously or intermittently in a concentration in which the total dose does not exceed a certain level, in consideration of the results of experimentation on animals and other various conditions. However, the dose may, of course, be properly varied depending on the administration route, the condition of the patient or animal to be treated (for example, age, body weight, sex, sensitivity, diet and the like), the interval between the administration of the drug used in combination with said compounds and the degree of disease. An optimum dose and the number of administrations under certain conditions should be determined by medical specialists.

For oral administration some compounds can be formulated into solid or liquid preparations such as capsules, pills, tablets, lozenges, melts, powders solutions, suspensions or emulsions. The solid unit dosage forms are those generally employed such as capsules or tablets. Capsules can be of the ordinary gelatin type containing additional excipients, such as, surfactants, lubricants and inert fillers, such as lactose, sucrose, and cornstarch. The compounds of present invention can also be tableted with conventional tablet bases such as lactose, sucrose, and cornstarch in combination with binders, such as acacia, cornstarch or gelatin, disintegrating agents such as potato starch or alginic acid, and lubricants such as stearic acid or magnesium stearate.

For parenteral administration some compounds may be administered as injectable dosages of a solution or suspension of the compound in a physiologically acceptable diluent with a pharmaceutical carrier. Suitable diluents or carriers include sterile liquids such as water or oils, with or without the addition of surfactants or other pharmaceutically acceptable adjuvants. Illustrative of various oils which can be employed in the practice of this invention are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions. Among them water is the most preferred.

The following examples illustrate the present invention but are by no means limitative of the scope of the invention.

EXAMPLE 1

Synthesis of p-chloro-benzylamine

Ammonium formate (25 g), formic acid (18.4 g) and Raney nickel (1 g) was introduced into a three-neck flask. Stirred and heated to a temperature of 125°–130° C., and within half an hour p-chloro-benzaldehyde (3.79 g) was added dropwise. The temperature was then increased for a period of 3 hours to 140°–150° C.

After cooling the pH of the mixture was adjusted to less than pH 3 by the addition of concentrated hydrochloric acid.

The resulting solution was refluxed for 3 hours. After cooling, the reaction mixture was made strongly alkaline by the addition of sodium hydroxide solution and then steam distilled.

The distillate was collected into a mixture of concentrated hydrochloric acid (18% W/V) and water (1:1). The solvent was distilled off and the residue was made strongly alkaline by the addition of sodium hydroxide solution.

The resulting mixture was extracted with chloroform, washed with water and dried over anhydrous magnesium sulfate. The chloroform was then distilled off, and the residue was purified by distillation whereupon the desired product was obtained as a colorless oil.

yield: 51–67%

Derivatives of benzylamine were synthesized using similar methods as the one described above, but using the corresponding benzaldehyde in place of p-chlorobenzaldehyde. When the starting material is a nitro-substituted benzaldehyde, there is no need to add Raney Ni in the reaction system, and steam distillation can not be used as described above. Extraction of the alkaline solution into chloroform replaces steam distillation.

EXAMPLE 2

Synthesis of furfuryl Amine

Furfuraldehyde oxime (10 g), obtained in a conventional way, was added to a solution of a mixture of 75 ml of 95% ethanol and 80 ml of acetic acid, and heated, using a water bath. Then 70 g of zinc powder, divided into four equal parts was added under stirring over a period of 5 hours.

The reaction mixture was allowed to stand over night and then poured into 400 ml of water. The residue of zinc powder was filtered off. The filtrate was made alkaline by the addition of sodium hydroxide solution, extracted with diethyl ether and dried over sodium hydroxide. The ether was distilled off and the product was purified by distillation with a boiling point of 143°–144° C.

yield: 56–63%

EXAMPLE 3

Synthesis of 4-chloro-1,2-di(aminomethyl) benzene 4-chloro-o-xylene (0.1 mole) was dissolved in anhydrous tetra-chloro-methane and refluxed with N-bromo-succinimide (40 g) and benzoyl peroxide (0.5 g) for 1.5 hours. After cooling and filtration tetrachloromethane was distilled off and dimethyl formamide (100 ml) and sodium phthalimidate (30 g) were added. The reaction mixture was maintained at a temperature ranging from 90° to 100° C. for 2 hours. After cooling 500 ml of water was added to the reaction mixture and then the mixture was extracted with chloroform three times. The chloroform extracts were combined and washed with water and a solution of sodium hydroxide. After drying the chloroform was distilled off until the first crystals began to appear, at this point the mixture was allowed to stand in order to complete recrystallization. 4-chloro-1,2-di(phthalimido-methyl)-benzene was obtained as a colorless crystalline product.

To 100 ml of the above said product (0.5 mole) diethyl ether and hydrazine hydrate (0.1 ml) were added. The mixture was refluxed for 2 hours and after this time period concentrated hydrochloric acid (50 ml) was added and the mixture was refluxed for a further 2 hours. The mixture was then cooled to a temperature of 0° C. and filtered, and the filtrate was concentrated under reduced pressure until a dry solid was obtained. The above said solid product was recrystallized using dilute hydrochloric acid.

4-chloro-1,2-di(aminomethyl)benzene was obtained. Total yield: 48–55%

A series of derivatives of bis(aminomethyl)benzene can be prepared in a similar manner by using the corresponding substituted o-xylene as a starting material.

EXAMPLE 4

Synthesis of [R:R] (−) and [S:S] (+)-4-phenyl-5-amino-1,3-dioxane

Trans-4-phenyl-5-chloro-1,3-dioxone (0.5 mol) was added into a high pressure vessel. It was subjected to amination after a two molar equivalent of ammonia gas was introduced into the vessel with methanol as the solvent under 100 atmospheres. Cis-4-phenyl-5-amino-1,3-dioxane was obtained by a conventional after-treatment. b.p. 170°-172° C./4 mmHg, yield: 72%.

The above said cis-4-phenyl-5-amino-1,3-dioxane was reacted with tartaric acid and recrystallized from water four times. It was redissolved in water and the solution was made alkaline by the addition of sodium hydroxide solution extracted with diethyl ether and dried over $MgSO_4$.

After drying the solvent was distilled off. The residue was then distilled at reduced pressure to obtain [R:R] (−)-4-phenyl-5-amino-1,3-dioxan, $[\alpha]_D^{16} = -65.2°$ the yield after circular treatment: more than 95%.

The aqueous filtrates obtained from the above reaction with tartaric acid and subsequent recrystallizations were combined and concentrated to dryness. The residue was recrystallized six times from methanol. The crystals obtained were dissolved in a 20% solution of sodium hydroxide, extracted with diethyl ether and the extracts were subsequently dried. The diethyl ether was distilled off and the residue was subjected to distillation under reduced pressure to obtain [S:S] (+)-4-phenyl-5-amino-1,3-dioxane, $[\alpha]_D^{16} = +62°$. The yield after circular treatment is more than 95%.

EXAMPLE 5

Synthesis of cis-platinum (II) di-(o-chlorobenzyl) amin diiodide

Potassium platinum chloride (8.3 g 20 mmole) was dissolved in water (200 ml). A saturated solution of potassium iodide was added. The mixture was heated in a water bath until the reaction mixture reached a temperature of 70° C. at which point heating was stopped and the reaction mixture was allowed to stand in the water bath until it reached room temperature, and placed in the dark for half an hour, then subsequently filtered. A chloro-benzyl amine (44 mmole) was then added to the filtrate. The mixture was maintained at 30° C. and stirred until it became colorless. The resultant precipitate was filtered and subsequently washed with water, ethanol, anhydrous ethanol and dried in the vacuum. The purified compound obtained following the above mentioned method was identified to be platinum (II) di-(o-chloro-benzyl) amine diiodide.

If further purification is necessary this can be achieved by dissolving said product in dimethyl formamide and adding a mixture of ethanol and water (1:1) in order to recrystallize the compound. After filtering, the crystals were subsequently washed with water and then with ethanol and finally with anhydrous ethanol and dried in vacuum. Product yield was 60-84%. The compounds listed in table (I) can be obtained in a similar way.

EXAMPLE 6

Synthesis of cis-platinum (II) di-(o-chloro-benzyl) amine dichloride

Cis-platinum (II) di-(o-chloro-benzyl) amine diiodide (5 g) obtained in the synthesis described in example 5 was stirred with sufficient amount of water to form a paste. Silver nitrate, in a quantity 4% stoichiometrially less than cis-platinum (II) di-(o-chlorobenzyl) amine diiodide was dissolved in water (50 ml) and added to the paste under stirring until silver ions ($Ag^+$) can no longer be detected in the solution. The reaction mixture was then filtered to remove silver iodide. Solid potassium chloride was added, such that it was in a 10% stoichiometric excess, to the filtrate.

The filtrate was stirred and allowed to stand for half an hour at room temperature. It was then put into a refrigerator and filtered after half an hour. The resultant product was dissolved in DMF. Crystals were separated by filtration after adding 0.1N hydrochloric acid to the solution. The filtrate was again put into the refrigerator and maintained therein for a further 2 hours. The resultant precipitate was filtered and subsequently washed with ice-water, anhydrous ethanol and anhydrous diethyl ether, and dried in a vacuum. The product obtained has a yellow color. The compounds listed in table (1) can be obtained in a manner similar to that in example 6 by using corresponding starting material.

EXAMPLE 7

Synthesis of platinum (II) di-(p-methoxy-benzyl) amine dichloride

Potassium chloride (4.2 g, 10 mmole) was dissolved in water (50 ml). The solution was filtered to remove non-soluble substances present, then p-methoxy benzylamine (20 mmole) was added to the filtrate. The mixture was maintained at a temperature of 30° C. and stirred until the solution became colorless. The resultant precipitate was filtered and subsequently dissolved in DMF. This solution was then filtered to remove any non-soluble Magnus salt. Crystals were obtained after adding water to the solution. The crystals were filtered and subsequently washed with water and ethanol, and dried in a vacuum.

EXAMPLE 8 the following complexes were prepared by following a synthesis similar to that described in example 6 using the appropriate starting materials.

platinum (II) di-[R-(+)-α-phenyl-ethyl] amine diiodide,
platinum (II) di-[R-(+)-α-phenyl-ethyl] amine dichloride;
platinum (II) di-[S-(−)-α-phenyl-ethyl] amine diiodide;
platinum (II) di-[s-(−)-α-phenyl-ethyl] amine dichloride;
platinum (II) di-[dl-α-phenyl-ethyl] amine diiodide;
platinum (II) di-[dl-α-phenyl-ethyl] amine dichloride;
and similarly the complexes shown in table 2.

EXAMPLE 9

The following complexes were prepared by following a synthesis similar to that described in example 6 using the appropriate starting materials.

platinum(II) di-[(R:R)-(−)-4-phenyl-1,3-dixoan-5-yl]amine diiodide;
platinum(II) di-[(R:R)-(−)-4-phenyl-1,3-dixoan-5-yl]amine dichloride;
platinum(II) di-[(S:S)-(+)-4-phenyl-1,3-dixoan-5-yl]amine diiodide;
platinum(II) di-[(S:S)-(+)-4-phenyl-1,3-dixoan-5-yl]amine dichloride.

EXAMPLE 10

The following complexes were prepared following a synthesis similar to that described in example 6 using the appropriate starting materials.

platinum (II)-di-[furfuryl] amine diiodide and;
platinum (II)-di-[furfuryl] amine dichloride.

EXAMPLE 11

Any of the compounds listed in Table II can be prepared using an stoichiometric amount of a corresponding nitrogen containing heteroaryl compound as a staring material and following a synthesis similar to that described in example 6.

EXAMPLE 12

The compounds listed in table III can be prepared using an stoichiometric amount of the corresponding 1,2-di(aminomethyl) benzene as a starting material and following a synthesis similar to that described in example 6.

EXAMPLE 13

The compounds 3, 5, 7, 9, 11, 13, 15, 17, 20, 22, 24, 26, 28, 30, 36, 38, 42, 44, 46, 48, 50, 52 listed in the table I can be prepared following a synthesis similar to the one described in example 6 with the modification of using potassium bromide instead of potassium iodide.

EXAMPLE 14

To the reaction mixture of the corresponding platinum (II) diamine diiodine compound, obtained by following the synthesis described in example 6, one of the following was added silver acetate, silver chloro-acetate, silver oxalate, silver malonate, silver hydroxy-1,2-benzenedicarboxylate, and silver gluconate. The pricipitate of silver iodide was then filtered off and the filtrate evaporated under reduced pressure. Thus the corresponding desired compound listed in table 5 was obtained.

EXAMPLE 15

Synthesis of platinum (IV) trans-dihydroxy-cis-di-[p-chlorobenzyl] amine dichloride Hydrogen peroxide in a 30% stoichiometric excess was added to the platinum (II) di-[p-chlorobenzyl]-amine-dichloride obtained following the synthesis described in example 7. The reaction mixture was heated using a water bath at 95° C. for 5 minutes. The precipitate was separated, filtered and subsequently washed with water and diethyl ether. The crystalline product was recrystallized from DMF, whereupon a yellowish solid was obtained. In a similar way other corresponding compounds listed in the table 4, can be obtained using the appropriate starting materials.

I claim:

1. A compound of the formula

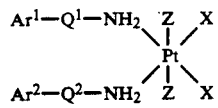

wherein
$Q^1$ and $Q^2$ may be the same or different and each is a number selected from the group consisting of methylene, ethylidene, dimethylene and substituted dimethylene;
$Ar^1$ and $Ar^2$ may be the same or different and each is selected from the group consisting of phenyl and substituted phenyl, or together form a divalent aromatic group selected from the group consisting of phenylene and substituted phenylene;
X is an anion ligand selected from the group consisting of chloride and iodide; and
Z is nothing or hydroxyl.

2. The compound of claim 1 wherein the substituent in said substituted dimethylene is hydroxyl.

3. The compound of claim 1 wherein the substituent in said substituted phenyl is one or more selected from the group consisting of hydroxyl, carboxyl, nitro, fluorine atom, chlorine atom and bromine atom.

4. The compound of claim 1 wherein said substituted phenyl is one selected from the group consisting of p-hydroxylphenyl, p-carboxylphenyl, p-fluor phenyl, p-chlorophenyl, o- or p-bromophenyl, and 4-chloro-3-hydroxyphenyl.

5. The compound of claim 1 wherein the substituent in said substituted phenylene is selected from carboxyl, hydroxyl, fluorine atom, chlorine atom and bromine atom.

6. The compound of claim 1, 2, 3, 4 or 5 wherein $Ar^1$—$Q^1$—$NH_2$ is the same as $Ar^2$—$Q^2$—$NH_2$.

7. The compound of claim 1 wherein $Ar^1$ and $Ar^2$ each is a p-fluorophenyl group, $Q^1$ and $Q^2$ each is a methylene group, each Z is absent, and each X is a chloride or iodide.

8. The compound of claim 1 wherein X is iodide.

* * * * *